United States Patent

Bassler et al.

[11] Patent Number: 6,139,693
[45] Date of Patent: Oct. 31, 2000

[54] METHOD FOR OBTAINING HEXAMETHYLENE DIAMINE FROM MIXTURES CONTAINING HEXAMETHYLENE DIAMINE

[75] Inventors: Peter Bassler, Viernheim; Rolf Fischer, Heidelberg; Hermann Luyken, Ludwigshafen; Alwin Rehfinger, Mutterstadt; Guido Voit, Freinsheim, all of Germany

[73] Assignee: BASF Aktiengesellschaft Ludwigshafen, Germany

[21] Appl. No.: 09/367,070

[22] PCT Filed: Jan. 30, 1998

[86] PCT No.: PCT/EP98/00506

§ 371 Date: Aug. 9, 1999

§ 102(e) Date: Aug. 9, 1999

[87] PCT Pub. No.: WO98/34903

PCT Pub. Date: Aug. 13, 1998

[30] Foreign Application Priority Data

Feb. 7, 1997 [DE] Germany .......................... 197 04 612

[51] Int. Cl.[7] .............................. B01D 3/10; B01D 3/34; C07C 209/84; C07C 209/86
[52] U.S. Cl. ................................ 203/49; 203/59; 203/60; 203/79; 203/80; 203/99; 203/DIG. 19; 564/492; 564/498
[58] Field of Search .................................. 203/49, 60, 59, 203/79, 80, 92, 99, 95, DIG. 19; 564/498, 492

[56] References Cited

U.S. PATENT DOCUMENTS

| 2,208,598 | 7/1940 | Rigby ...................................... 260/464 |
| 2,762,835 | 9/1956 | Swerdloff ................................ 260/465 |
| 3,775,258 | 11/1973 | Kershaw ................................... 203/29 |
| 4,282,381 | 8/1981 | Buehler et al. ......................... 564/498 |
| 4,389,348 | 6/1983 | Diamond et al. ....................... 260/465 |
| 4,601,851 | 7/1986 | Bartmann et al. ...................... 252/522 |
| 4,601,859 | 7/1986 | Galle et al. .............................. 558/459 |
| 4,803,304 | 2/1989 | Smiley .................................... 564/498 |
| 5,133,838 | 7/1992 | Sieja ........................................ 203/91 |
| 5,961,788 | 10/1999 | Ostermaier ............................... 203/80 |

FOREIGN PATENT DOCUMENTS

| 077911 | 5/1983 | European Pat. Off. . |
| 161419 | 11/1985 | European Pat. Off. . |
| 848654 | 9/1952 | Germany . |
| 954416 | 12/1956 | Germany . |
| 1204681 | 4/1960 | Germany . |
| 4235466 | 4/1994 | Germany . |
| 19500222 | 7/1996 | Germany . |
| 4446893 | 7/1996 | Germany . |
| 19548289 | 6/1997 | Germany . |
| 731819 | 6/1955 | United Kingdom . |
| 92/21650 | 12/1992 | WIPO . |
| 93/01207 | 1/1993 | WIPO . |

*Primary Examiner*—Virginia Manoharan
*Attorney, Agent, or Firm*—Keil & Weinkauf

[57] ABSTRACT

A process for recovering hexamethylenediamine (I) from a mixture (II) including (I) hexamethylenediamine,
(III) hexamethyleneimine,
(IV) a compound selected from 2-aminomethylcyclopentylamine and 1,2-diaminocyclohexane,
(V) an imine,
(VI) adiponitrile and 6-aminocapronitrile includes distilling (a) a mixture (II) to obtain
  (a1) a low boiling fraction (III),
  (a2) a medium boiling fraction (VII) (I), (IV) and (V), and
  (a3) a high boiling fraction (V) and (VI),
(b) a mixture (VII) to obtain
  (b1) an overhead product (IV), and
  (b2) a mixture (VIII) (I) and (V) as bottom product, and
(c) a mixture (VIII) to obtain
  (c1) (I) as overhead product, and
  (c2) a bottom product (V).

11 Claims, No Drawings

METHOD FOR OBTAINING HEXAMETHYLENE DIAMINE FROM MIXTURES CONTAINING HEXAMETHYLENE DIAMINE

DESCRIPTION

The present invention relates to a process for recovering hexamethylenediamine (I) from a mixture (II) comprising (I) hexamethylenediamine, (III) hexamethyleneimine, (IV) a compound selected from the group consisting of 2-aminomethylcyclopentylamine and 1,2-diaminocyclohexane, (V) an imine, (VI) adiponitrile and 6-aminocapronitrile, which comprises distilling (a) a mixture (II) to obtain
  (a1) a low boiling fraction comprising essentially (III),
  (a2) a medium boiling fraction (VII) comprising (I), (IV) and (V), and
  (a3) a high boiling fraction comprising (V) and (VI), (b) a mixture (VII) to obtain
  (b1) an overhead product comprising essentially (IV), and
  (b2) a mixture (VIII) comprising (I) and (V) as bottom product, and (c) a mixture (VIII) to obtain
  (c1) (I) as overhead product, and
  (c2) a bottom product comprising the essential portion of (V).

It is known, for example from: K. Weissermel, H.-J. Arpe, Industrielle Organische Chemie, 4th Edition, page 270, VCH-Verlagsgesellschaft, to fully hydrogenate adiponitrile in the presence of iron, cobalt or nickel catalysts to form the fiber intermediate hexamethylenediamine. As a consequence of the quantitative conversion of the adiponitrile into hexamethylenediamine, the hydrogenation effluent contains virtually no adiponitrile and no 6-aminocapronitrile.

The hexamethylenediamine can be purified to fiber grade quality in a conventional manner, for example by distillation as described in GB-A-731 819 or by crystallization as described in U.S. Pat. No. 4,282,381.

It is further known to hydrogenate adiponitrile partially to mixtures of the two fiber intermediates 6-aminocapronitrile and hexamethylenediamine and also unconverted adiponitrile, for example according to U.S. Pat. No. 4,601,8591, U.S. Pat. No. 2,762,835, U.S. Pat. No. 2,208,598, DE-A 848 654, DE-A-44 46 893, DE-A-954 416, DE-A-42 35 466, WO 92/21650, DE-A-19 500 222 or German Application 19 548 289.1, in the presence of nickel, cobalt, iron, ruthenium or rhodium catalysts.

6-Aminocapronitrile can be cyclized to form caprolactam or be polymerized directly to form nylon-6.

The partial hydrogenation gives rise to byproducts which are difficult to separate from hexamethylenediamine such as hexamethyleneimine, 1,2-diaminocyclohexane and 2-aminomethylcyclopentylamine. Tetrahydroazepine and the two cyclic diamines in particular reduce the quality of nylon-6,6 produced from such impure hexamethylenediamine, for example the color quality. For this reason, the impurities mentioned have to be removed from the hexamethylenediamine down to a residual level of a few ppm.

The processes known for the purification of hexamethylenediamine from the full hydrogenation of adiponitrile cannot be used for the reaction mixture obtained from the partial hydrogenation of adiponitrile because of the higher levels of these byproducts, the different mixing ratios of the byproducts and also the presence of 6-aminocapronitrile and adiponitrile.

It is an object of the present invention to provide a process for recovering hexamethylenediamine from an adiponitrile partial hydrogenation mixture comprising hexamethylenediamine, 6-aminocapronitrile and adiponitrile in a technically simple and economical manner.

We have found that this object is achieved by the process described at the beginning.

Mixtures (II) can be obtained in a conventional manner by partial hydrogenation of adiponitrile, for example according to a process as described in EP-A-161 419, EP-A-77 911, U.S. Pat. No. 4,389,348, U.S. Pat. No. 4,601,859, WO 93/1207, DE-A 42 35 466, U.S. Pat. No. 2,762,835, U.S. Pat. No. 2,208,598, DE-A 848 654, DE-A-44 46 893, DE-A-954 416, DE-A-42 35 466, WO 92/21650, DE-A 19 500 222 and German Application 19 548 289.1 by, in general, conducting the hydrogenation in the presence of nickel, cobalt, iron, rhodium or ruthenium catalysts. The catalysts may be employed in the form of supported or unsupported catalysts. Examples of suitable catalyst supports are aluminum oxide, silicon dioxide, titanium dioxide, magnesium oxide, active carbons and spinels. Examples of unsupported catalysts are Raney nickel and Raney cobalt.

If the hydrogenation was carried out using liquid diluents, such as ammonia, these can be removed in a conventional manner, for example as described in DE-A-19 500 222.

The mixtures (II) generally comprise hexamethylenediamine (I), especially in amounts from 5 to 90% by weight based on (II), hexamethyleneimine (III), especially in amounts from 0.1 to 10% by weight based on (II), a compound (IV) selected from the group consisting of 2-aminomethylcyclopentylamine and 1,2-diaminocyclohexane or mixtures thereof, especially in amounts from 5 ppm to 5% by weight based on (II), an imine (V) or mixtures of such imines, such as tetrahydroazepine, in which case the imines can be present as individual compounds or as adducts, especially with amines such as hexamethylenediamine or 6-aminocapronitrile, and such adducts shall for the purposes of the present invention likewise be termed imines (V), especially in amounts from 5 to 10,000 ppm based on (II)

adiponitrile and 6-aminocapronitrile (VI), the 6-aminocapronitrile content being from 5 to 90% by weight based on (II) and the adiponitrile content being from 5 to 90% by weight based on (II).

According to the invention, the mixture (II) is subjected to a distillation (a).

This distillation affords as low boiling fraction essentially hexamethyleneimine (III). This low boiling fraction (a1) can contain further compounds, such as residues of the liquid diluent, for example ammonia, used in the hydrogenation or residues of the water produced as byproduct in the hydrogenation.

The medium boiling fraction (a2) obtained is a mixture (VII) comprising essentially hexamethylenediamine (I), a compound (IV) and a compound (IVb), the level of hexamethylenediamine in the mixture (VII) being preferably within the range from 80 to 100% by weight based on (VII), the level of compound (IV) in the mixture (VII) being preferably within the range from 5 ppm to 0.5% by weight based on (VII) and the level of compound (IVb) in the mixture (VII) being preferably within the range from 1 to 10,000 ppm based on (VII).

The high boiling fraction (a3) obtained is a mixture (VI) comprising essentially adiponitrile and 6-aminocapronitrile, from which adiponitrile and 6-aminocapronitrile can be recovered, preferably by distillation. The adiponitrile may advantageously be recycled into the partial hydrogenation described.

Suitable apparatus for the distillation is any customary distillation column, as described for example in: Kirk-Othmer, Encyclopedia of Chemical Technology, 3rd Ed., Vol. 7, John Wiley & Sons, New York, 1979, pages 870–881, such as sieve plate columns, bubble cap columns or columns packed with arranged or dumped packing.

Preference is given to distillation apparatus having a pressure drop from the bottom to the top of from 1 to 500 mbar, preferably from 5 to 50 mbar, the pressure in the bottom being advantageously within the range from 1 to 500 mbar and the pressure at the top being advantageously within the range from 1 to 500 mbar. This results in bottom temperatures from 100 to 300° .C, especially from 150 to 250° C.

The distillation can be carried out in a plurality of columns, such as 2 or 3 or more, but is preferably carried out in a single column.

If the distillation is carried out in one column, it is advantageous to obtain (a1) as overhead product, (a2) as sidestream takeoff and (a3) as bottom product.

If the separation is carried out in two columns, it is advantageous to obtain a mixture of (a1) and (a2) as overhead product of the first column and to separate this mixture in the second column, so that (a1) is obtained as overhead product of the second column.

The distillation mixture advantageously has an average mean residence time of at least 5 minutes, preferably at least 15 minutes, especially at least 45 minutes, on at least one, preferably from 1 to 15, particularly preferably from 1 to 7, especially 1, 2 or 3, levels of the distillation column.

It is preferable to withdraw the distillation mixture from the distillation column on at least one level, pass it through a delay vessel and return it into the distillation column. The returning can take place onto the withdrawal level or onto a level above or below the withdrawal level.

It is advantageous for the distillation column reflux to pass first through a delay vessel before it is returned into the distillation column.

The withdrawing of distillation liquid from the column, the passing through the delay vessel, the returning into the distillation column and, optionally, the recirculating of the liquid in the delay vessel may all be effected using conventional apparatus, such as pumps, in which case the returning may take place onto the withdrawal level of the distillation column, especially in the case of a plate column, or onto a level which is above, especially in the case of an arranged-packing column, or below the withdrawal level.

The distillation of mixture (II) can be carried out with advantage by addition of a compound (IX) which is inert to the components of the mixture under the distillation conditions and whose boiling point under the distillation conditions is above the boiling point of the medium boiling fraction (a2).

Suitable compounds (IX) include aromatics, aliphatics, such as acyclic and cyclic aliphatics, and aliphatic-aromatic compounds. These compounds can bear substituents, such as an alkyl, aryl, cycloalkyl, aralkyl, ester, amide, nitrile or amino group, preferably a nitrile or amino group, or a plurality of identical or different such groups.

The compound (IX) can consist of one compound or mixtures of such compounds.

It is advantageous to use compounds (IX) which are simple to convert, as by hydrogenation, for example with a gas comprising molecular hydrogen in the presence of a catalyst, into hexamethylenediamine or 6-aminocapronitrile.

The products obtained in this reaction can advantageously be used afresh in the process of the invention. The distillation affords, preferably as bottom product, a mixture comprising a compound (IX).

If the mixture additionally comprises hexamethylenediamine (I), it is advantageously possible to reduce the bottom temperature of the distillation.

The compound (IX) can be recovered from the mixture in a conventional manner, for example by physical processes, such as distillation or extraction, or chemical processes, such as chemisorption or hydrogenation.

This compound (IX) obtained from the mixture can advantageously be returned into steps (a) or (c) or both steps. The difference in the boiling points between the medium boiling fraction (a2) and the compound (IX) should be from 1 to 200° C., preferably from 5 to 100° C., under the distillation conditions. The use of adiponitrile or 6-aminocapronitrile or mixtures thereof is particularly advantageous.

The compound (IX) can be added to the mixture (II) before or during the distillation.

The addition of compound (IX) to the mixture (II) before the distillation can be effected in a conventional manner in customary mixing apparatus.

The addition of compound (IX) to the mixture (II) during the distillation can be effected by feeding the compound (IX) into the distillation apparatus, preferably into the bottom region.

The distillation of mixture (II) can be carried out with advantage in the presence of carbon dioxide.

Carbon dioxide can be added to the distillation mixture before or preferably during the distillation in the form of a compound which releases carbon dioxide under the distillation conditions, such as ammonium carbonate, ammonium carbamate or urea or mixtures thereof, in which case these compounds can be added in pure form or in a liquid diluent, as in one or more constituents of mixture (II), or in the form of solid, liquid or preferably gaseous carbon dioxide, for example in the form of a gas comprising carbon dioxide or especially in the form of pure gaseous carbon dioxide which comprises only the customary impurities. The carbon dioxide content of the distillation mixture should be from 0.1 to 1000 mol of carbon dioxide per mole of imine function of the imines, such as tetrahydroazepine.

According to the invention, the mixture (VII) is subjected to a distillation (b).

This distillation produces as overhead product (b1) a compound (IV) comprising essentially 2-aminomethylcyclopentylamine, 1,2-diaminocyclohexane or mixtures thereof. In addition, the overhead product may comprise hexamethyleneimine or hexamethylenediamine or mixtures thereof.

The bottom product (b2) of the distillation column is a mixture (VIII) comprising essentially hexamethylenediamine (I) and an imine (V), the hexamethylenediamine content of the mixture (VIII) being preferably within the range from 50 to 100% by weight based on (VIII).

Suitable apparatus for the distillation is any customary distillation column, as described for example in: Kirk-Othmer, Encyclopedia of Chemical Technology, 3rd Ed., Vol. 7, John Wiley & Sons, New York, 1979, pages 870–881, such as sieve plate columns, bubble cap columns or columns packed with arranged or dumped packing.

Preference is given to distillation apparatus having a pressure drop from the bottom to the top of from 0 to 200 mbar, preferably from 0 to 50 mbar, the pressure in the bottom being advantageously within the range from 3 to 300 mbar, especially form 1 to 200 mbar, and the pressure at the top being advantageously within the range from 1 to 300 mbar, especially form 1 to 200 mbar. This results in bottom temperatures from 100 to 300° C., especially from 150 to 250° C.

The distillation can be carried out in a plurality of columns, such as 2 or 3 or more, but is preferably carried out in a single column.

Particularly suitable distillation columns are distillation columns which have a low pressure drop, preferably not more than 1 mbar, especially 0.3 mbar, per theoretical stage.

Especially suitable distillation columns are packed columns, preferably with arranged packing elements such as metal sheet packings, especially woven wire packings.

It is advantageous to add water to the distillation mixture, in which case water contents from 0.001 to 10, especially from 0.01 to 5% by weight of water, based on the distillation mixture are preferred.

The water can be added to the mixture before the distillation or during the distillation, for example in the lower region of the column.

According to the invention, mixture (VIII) is subjected to a distillation (c).

This distillation yields as overhead product (c1) hexamethylenediamine (I), advantageously in a purity suitable for fiber production.

The bottom product (c2) comprises essential parts of (V) and also other compounds which have a higher boiling point than hexamethylenediamine.

Suitable apparatus for the distillation is any customary distillation column, as described for example in: Kirk-Othmer, Encyclopedia of Chemical Technology, 3rd Ed., Vol. 7, John Wiley & Sons, New York, 1979, pages 870–881, such as sieve plate columns, bubble cap columns or columns packed with arranged or dumped packing.

Preference is given to distillation apparatus having a pressure drop from the bottom to the top of from 1 to 1000 mbar, preferably from 1 to 500 mbar, the pressure in the bottom being advantageously within the range from 10 to 900 mbar and the pressure at the top being advantageously within the range from 50 to 500 mbar. This results in bottom temperatures from 100 to 300° C., especially from 150 to 250° C.

The distillation can be carried out in a plurality of columns, such as 2 or 3, but is preferably carried out in a single column.

The distillation mixture advantageously has an average mean residence time of at least 5 minutes, preferably at least 15 minutes, especially at least 45 minutes, on at least one, preferably from 1 to 15, particularly preferably from 1 to 7, especially 1, 2 or 3, levels of the distillation column.

It is preferable to withdraw the distillation mixture from the distillation column on at least one level, pass it through a delay vessel and return it into the distillation column. The returning can take place onto the withdrawal level or onto a level above or below the withdrawal level. It is advantageous for the distillation column reflux to pass first through a delay vessel before it is returned into the distillation column.

The withdrawing of distillation liquid from the column, the passing through the delay vessel, the returning into the distillation column and, optionally, the recirculating of the liquid in the delay vessel may all be effected using conventional apparatus, such as pumps, in which case the returning may take place onto the withdrawal level of the distillation column, especially in the case of a plate column, or onto a level which is above, especially in the case of an arranged-packing column, or below the withdrawal level. The distillation of mixture (VIII) can be carried out with advantage by addition of a compound (X) which is inert to the components of the mixture under the distillation conditions and whose boiling point under the distillation conditions is above the boiling point of hexamethylenediamine (I).

Suitable compounds (X) include aromatics, aliphatics, such as acyclic and cyclic aliphatics, and aliphatic-aromatic compounds. These compounds can bear substituents, such as an alkyl, aryl, cycloalkyl, aralkyl, ester, amide, nitrile or amino group, preferably a nitrile or amino group, or a plurality of identical or different such groups.

Said compound (X) can consist of one compound or mixtures of such compounds.

It is advantageous to use compounds (X) which are simple to convert, as by hydrogenation, for example with a gas comprising molecular hydrogen in the presence of a catalyst, into hexamethylenediamine or 6-aminocapronitrile.

The products obtained in this reaction can advantageously be used afresh in the process of the invention. The distillation affords, preferably as bottom product, a mixture comprising a compound (X).

If the mixture additionally comprises hexamethylenediamine (I), it is advantageously possible to reduce the bottom temperature of the distillation.

The compound (X) can be recovered from the mixture in a conventional manner, for example by physical processes, such as distillation or extraction, or chemical processes, such as chemisorption or hydrogenation.

This compound (X) obtained from the mixture can advantageously be returned into steps (a) or (c) or both steps.

The difference in the boiling points between hexamethylenediamine (I) and the compound (X) should be from 1 to 200° C., preferably from 5 to 100° C., under the distillation conditions.

The use of adiponitrile or 6-aminocapronitrile or mixtures thereof is particularly advantageous.

The compound (X) can be added to the mixture (VIII) before or during the distillation.

The addition of compound (X) to the mixture (VIII) before the distillation can be effected in a conventional manner in customary mixing apparatus.

The addition of compound (X) to the mixture (VIII) during the distillation can be effected by feeding the compound (X) into the distillation apparatus, preferably into the bottom region.

The distillation of mixture (VIII) can be carried out with advantage in the presence of carbon dioxide.

Carbon dioxide can be added to the distillation mixture before or preferably during the distillation in the form of a compound which releases carbon dioxide under the distillation conditions, such as ammonium carbonate, ammonium carbamate or urea or mixtures thereof, in which case these compounds can be added in pure form or in a liquid diluent, as in one or more constituents of mixture (VIII), or in the form of solid, liquid or preferably gaseous carbon dioxide, for example in the form of a gas comprising carbon dioxide or especially in the form of pure gaseous carbon dioxide which comprises only the customary impurities. The carbon dioxide content of the distillation mixture should be from 0.01 to 1000 mol of carbon dioxide per mole of imine function of the imines, such as tetrahyroazepine.

We claim:

1. A process for recovering hexamethylenediamine (I) from a mixture (II) comprising (I) hexamethylenediamine, (III) hexamethyleneimine, (IV) a compound selected from the group consisting of 2-aminomethylcyclopentylamine and 1,2-diaminocyclohexane, (V) an imine, (VI) adiponitrile and 6-aminocapronitrile, which comprises:

(a) distilling a mixture (II) in a column at a pressure drop from the bottom to the top of from 1 to 500 mbar, a pressure in the bottom within the range from 1 to 500 mbar, a pressure at the top within the range from 1 to 500 mbar and a bottom temperature of from 100 to 300° C. to obtain
- (a1) a low boiling fraction comprising essentially (III) as overhead product,
- (a2) a medium boiling fraction (VII) comprising (I), (IV) and (V) as sidestream takeoff, and
- (a3) a high boiling fraction comprising (V) and (VI) as bottom product, (b) distilling the mixture (VII) to obtain
- (b1) an overhead product comprising essentially (IV), and
- (b2) a mixture (VIII) comprising (I) and (V) as bottom product, and (c) distilling the mixture (VIII) to obtain
- (c1) (I) as overhead product, and
- (c2) a bottom product comprising (V).

2. A process as claimed in claim 1, wherein the mean average residence time of the distillation mixture in a distillation apparatus is at least 5 minutes in step (a).

3. A process as claimed in claim 1, wherein the mean average residence time of the distillation mixture in a distillation apparatus is at least 5 minutes in step (c).

4. A process as claimed in claim 11, wherein carbon dioxide is added to the distillation in step (a).

5. A process as claimed in claim 1, wherein carbon dioxide is added to the distillation in step (c).

6. A process as claimed in claim 1, wherein a compound (IX) which is inert toward the components of the mixture under the distillation conditions and has a boiling point above the boiling point of hexamethylenediamine (I) is added to the distillation mixture in step (a).

7. A process as claimed in claim 1, wherein a compound (X) having a boiling point above the boiling point of the mixture (VII) is added to the distillation mixture in step (c).

8. A process as claimed in claim 7, wherein said compound (X) comprises the compound (VI).

9. A process as claimed in claim 7, wherein compound (X) is adiponitrile, 6-aminocapronitrile or a mixture thereof.

10. A process as claimed in claim 7, wherein said compound (X) comprises bottom product from (a3).

11. A process as claimed in claim 1, wherein water is added to the distillation mixture in step (b).

* * * * *

UNITED STATES PATENT AND TRADEMARK OFFICE
CERTIFICATE OF CORRECTION

PATENT NO. : 6,139,693
DATED : October 31, 2000
INVENTOR(S) : Bassler et al.

Page 1 of 1

It is certified that error appears in the above-identified patent and that said Letters Patent is hereby corrected as shown below:

<u>Column 8,</u>
Line 10, delete "claim 11" and substitute -- claim 1 --.

Signed and Sealed this

Eleventh Day of September, 2001

Attest:

*Nicholas P. Godici*

NICHOLAS P. GODICI
*Attesting Officer*  *Acting Director of the United States Patent and Trademark Office*